(12) United States Patent
Furno et al.

(10) Patent No.: US 8,653,320 B2
(45) Date of Patent: *Feb. 18, 2014

(54) DEODORIZING SUPER-ABSORBENT COMPOSITION

(75) Inventors: Franck Furno, Düsseldorf (DE); Felix Müller, Velbert (DE); Jörg Peggau, Essen (DE); Michael Keup, Datteln (DE); Harald Schmidt, Tonisvorst (DE)

(73) Assignee: Evonik Degussa GmbH, Essen (DE)

( * ) Notice: Subject to any disclaimer, the term of this patent is extended or adjusted under 35 U.S.C. 154(b) by 1098 days.

This patent is subject to a terminal disclaimer.

(21) Appl. No.: 12/093,548

(22) PCT Filed: Nov. 17, 2006

(86) PCT No.: PCT/EP2006/011055
§ 371 (c)(1),
(2), (4) Date: Nov. 18, 2008

(87) PCT Pub. No.: WO2007/057203
PCT Pub. Date: May 24, 2007

(65) Prior Publication Data
US 2010/0035757 A1 Feb. 11, 2010

(30) Foreign Application Priority Data
Nov. 18, 2005 (DE) .......................... 10 2005 055 497

(51) Int. Cl.
*A61F 13/15* (2006.01)
*A61F 13/20* (2006.01)
*A61K 9/50* (2006.01)
*A61K 47/30* (2006.01)

(52) U.S. Cl.
USPC ......... 604/358; 604/367; 424/501; 514/772.3

(58) Field of Classification Search
USPC ................ 424/501; 514/772.3; 604/358, 367
See application file for complete search history.

(56) References Cited

U.S. PATENT DOCUMENTS

| | | | |
|---|---|---|---|
| 4,076,663 A | 2/1978 | Masuda et al. | |
| 4,131,576 A | 12/1978 | Iovine et al. | |
| 4,172,123 A | 10/1979 | Smart et al. | |
| 4,179,367 A | 12/1979 | Barthell et al. | |
| 4,286,082 A | 8/1981 | Tsubakimoto et al. | |
| 4,340,706 A | 7/1982 | Obayashi et al. | |
| 4,587,308 A | 5/1986 | Makita et al. | |
| 4,766,173 A | 8/1988 | Bailey et al. | |
| 4,857,610 A | 8/1989 | Chmelir et al. | |
| 4,893,999 A | 1/1990 | Chmelir et al. | |
| 5,045,322 A | 9/1991 | Blake et al. | |
| 5,409,771 A | 4/1995 | Dahmen et al. | |
| 5,610,220 A | 3/1997 | Klimmek et al. | |
| 5,672,633 A | 9/1997 | Brehm et al. | |
| 5,712,316 A | 1/1998 | Dahmen et al. | |
| 5,807,364 A * | 9/1998 | Hansen ........................ 604/367 |
| 5,849,816 A * | 12/1998 | Suskind et al. ............... 523/201 |
| 6,060,557 A | 5/2000 | Dahmen et al. | |
| 6,403,700 B1 | 6/2002 | Dahmen et al. | |
| 6,492,574 B1 * | 12/2002 | Chen et al. .................... 604/378 |
| 6,605,673 B1 | 8/2003 | Mertens et al. | |
| 6,620,889 B1 | 9/2003 | Mertens et al. | |
| 6,623,848 B2 | 9/2003 | Brehm et al. | |
| 6,831,142 B2 | 12/2004 | Mertens et al. | |
| 6,911,572 B1 | 6/2005 | Bruhn et al. | |
| 6,916,465 B2 | 7/2005 | Panzer et al. | |
| 6,958,429 B2 | 10/2005 | Bruhn et al. | |
| 7,144,957 B2 | 12/2006 | Funk et al. | |
| 7,179,862 B2 | 2/2007 | Mertens et al. | |
| 7,226,584 B2 | 6/2007 | Lersch et al. | |
| 7,285,599 B2 | 10/2007 | Mertens et al. | |
| 7,541,395 B2 | 6/2009 | Reimann et al. | |
| 7,572,864 B2 | 8/2009 | Mertens et al. | |
| 7,625,957 B2 * | 12/2009 | Harren et al. ................. 523/122 |
| 7,728,079 B2 | 6/2010 | Harren et al. | |
| 2003/0135172 A1 | 7/2003 | Whitmore et al. | |
| 2003/0207997 A1 | 11/2003 | Mertens et al. | |
| 2003/0220211 A1 * | 11/2003 | Stoddart et al. ............... 510/101 |
| 2004/0024374 A1 | 2/2004 | Hjorth et al. | |
| 2005/0171235 A1 | 8/2005 | Harren et al. | |

(Continued)

FOREIGN PATENT DOCUMENTS

| | | |
|---|---|---|
| DE | 2612846 | 2/1978 |
| DE | 2706135 A1 | 8/1978 |

(Continued)

OTHER PUBLICATIONS

F.L. Buchholz, "Absorbency and Superabsorbency," Chapter 1, Modern Superabsorbent Polymer Technology, Copyright 1998, pp. 1-17, Wiley-VCH, New York.
Furno et al., U.S. Appl. No. 12/679,631, filed Mar. 23, 2010.
German language International Search Report mailed on Aug. 13, 2010 in PCT/EP2008/008081.
German language Written Opinion mailed on Aug. 13, 2010 in PCT/EP2008/008081.
German language Written Opinion mailed on Jun. 12, 2009 in PCT/EP2009/052347.
Harren et al., U.S. Appl. No. 12/600,964, filed Dec. 15, 2009.
International Search Report mailed on Jun. 12, 2009 in PCT/EP2009/052347.
International Search Report mailed on Oct. 26, 2007 in PCT/EP2006/011055.
English translation of International Preliminary Report on Patentability completed on Jan. 25, 2008 in PCT/ EP2006/011055.

*Primary Examiner* — Abigail Fisher
(74) *Attorney, Agent, or Firm* — Philip P. McCann; John P. Zimmer; Smith Moore Leatherwood LLP

(57) ABSTRACT

The invention relates generally to an odor-absorbing superabsorbing composition, a process for production of an odor-absorbing superabsorbing composition, a composite comprising an odor-absorbing superabsorbing composition, a hygiene article comprising a composite, chemical products comprising or based on an odor-absorbing superabsorbing composition or a composite, as well as the use of an odor-absorbing superabsorbing composition or of a composite in chemical products.

12 Claims, 2 Drawing Sheets

(56) References Cited

U.S. PATENT DOCUMENTS

| | | | |
|---|---|---|---|
| 2006/0029567 | A1 | 2/2006 | Dutkiewicz |
| 2006/0029782 | A1 | 2/2006 | Harren et al. |
| 2006/0057389 | A1 | 3/2006 | Reimann et al. |
| 2007/0015860 | A1 | 1/2007 | Frank |
| 2007/0066754 | A1 | 3/2007 | Loeker et al. |
| 2007/0129495 | A1 | 6/2007 | Mertens et al. |
| 2007/0260357 | A1 | 11/2007 | Issberner et al. |
| 2008/0221277 | A1 | 9/2008 | Walden et al. |
| 2008/0280128 | A1 | 11/2008 | Furno et al. |
| 2009/0023006 | A1 | 1/2009 | Bub et al. |
| 2009/0105389 | A1 * | 4/2009 | Walden et al. ............ 524/437 |
| 2009/0130040 | A1 | 5/2009 | Jonchiere |
| 2009/0134357 | A1 | 5/2009 | Bub et al. |
| 2009/0202805 | A1 | 8/2009 | Furno et al. |
| 2009/0209683 | A1 | 8/2009 | Reimann et al. |
| 2009/0227741 | A1 | 9/2009 | Walden et al. |
| 2009/0239995 | A1 | 9/2009 | Bub et al. |
| 2010/0036004 | A1 | 2/2010 | Harren et al. |
| 2010/0057027 | A1 | 3/2010 | Furno et al. |
| 2010/0099799 | A1 | 4/2010 | Fricker et al. |
| 2010/0105808 | A1 | 4/2010 | Fricker et al. |
| 2010/0105809 | A1 | 4/2010 | Fricker et al. |
| 2010/0119830 | A1 | 5/2010 | Braig et al. |

FOREIGN PATENT DOCUMENTS

| | | | |
|---|---|---|---|
| DE | 2840010 | | 6/1979 |
| DE | 3503458 | | 8/1985 |
| DE | 3544770 | | 6/1987 |
| DE | 3713601 | | 11/1988 |
| DE | 3816252 | A1 | 11/1988 |
| DE | 4020780 | C1 | 8/1991 |
| DE | 4323001 | | 7/1993 |
| DE | 4244548 | | 7/1994 |
| DE | 4418818 | | 1/1995 |
| DE | 4333056 | | 3/1995 |
| DE | 19518645 | C1 | 9/1996 |
| DE | 19529348 | A1 | 2/1997 |
| DE | 19825486 | A1 | 2/2000 |
| DE | 19909653 | A1 | 9/2000 |
| DE | 19909838 | A1 | 9/2000 |
| DE | 19939662 | A1 | 2/2001 |
| DE | 10160933 | A1 | 6/2003 |
| DE | 10334271 | A1 | 2/2005 |
| DE | 102005055497 | A1 | 5/2007 |
| EP | 0532002 | | 3/1993 |
| EP | 0889063 | | 1/1999 |
| EP | 1358894 | A1 | 11/2003 |
| JP | 60158861 | | 1/1984 |
| WO | 96/05234 | A1 | 2/1996 |
| WO | 96/31644 | A1 | 10/1996 |
| WO | 99/34843 | A1 | 7/1999 |
| WO | 00/71176 | A1 | 11/2000 |
| WO | 0130748 | A1 | 5/2001 |
| WO | 01/70191 | A1 | 9/2001 |
| WO | 0170210 | A2 | 9/2001 |
| WO | 02/056812 | A1 | 7/2002 |
| WO | 03028778 | A2 | 4/2003 |
| WO | 2004/037903 | A2 | 5/2004 |
| WO | 2005/011860 | | 2/2005 |
| WO | 2007/057043 | A1 | 5/2007 |
| WO | 2007057203 | A2 | 5/2007 |
| WO | 2007122343 | A1 | 11/2007 |
| WO | 2010052182 | A1 | 5/2010 |

* cited by examiner

DEODORIZING SUPER-ABSORBENT COMPOSITION

This application is a national stage application under 35 U.S.C. 371 of international application No. PCT/EP2006/011055 filed 17 Nov. 2006, and claims priority to German Application No. DE 10 2005 055 497.0 filed 18 Nov. 2005, the disclosures of which are expressly incorporated herein by reference.

BACKGROUND

The invention relates in general to an odor-absorbing superabsorbing composition, a process for production of an odor-absorbing superabsorbing composition, a composite comprising an odor-absorbing superabsorbing composition, a hygiene article comprising a composite, chemical products comprising or based on an odor-absorbing superabsorbing composition or a composite, as well as the use of an odor-absorbing superabsorbing composition or of a composite in chemical products.

Superabsorbers are water-insoluble, crosslinked polymers, which are capable, by swelling and formation of hydrogels, of absorbing, and retaining under pressure, large amounts of aqueous liquids, in particular body fluids, preferably urine or blood. In general, these amounts of liquids amount to at least 10 times or even at least 100 times the dry weight of the superabsorber or of the superabsorbing composition in water. Because of these characteristic properties, these polymers principally find application in sanitary articles such as baby diapers, incontinence products or sanitary napkins. An encompassing overview of superabsorbers and superabsorbent compositions, their application and their production, is given by F. L. Buchholz and A. T. Graham (Editors) in "Modern Superabsorbent Polymer Technology," Wiley-VCH, New York, 1998.

The preparation of superabsorbers generally occurs by radical polymerization of acid groups-carrying, mostly partially neutralized monomers in the presence of crosslinkers. Through the selection of the monomer composition, the crosslinkers and the polymerization conditions and the processing conditions for the hydrogel obtained after polymerization, polymers with different absorbent properties can be produced. Further possibilities are offered by the production of graft polymers, for example using chemically modified starches, celluloses and polyvinyl alcohol according to DE-OS 26 12 846.

DE 40 20 780 C1 discloses the post-treatment of superabsorbing polymers by post-crosslinking of the surfaces of the polymer particles. Through the post-crosslinking of the surface of the water-absorbing polymer particles, in particular the absorption capacity of the polymer particles under the effect of pressure is increased.

DE 199 09 653 A1 and DE 199 09 838 A1 describe powdery, surface-post-crosslinked, water, aqueous or serous liquids- or blood-absorbing polymers, which are based on acid groups-carrying monomers and which have been coated and post-crosslinked with a surface post-crosslinking agent and a cation in aqueous solution. The polymers disclosed in this prior art have advantageous absorption properties compared to conventional polymers, in particular a high permeability.

When wearing hygiene articles comprising absorbent polymers for longer wearing times, in particular if these have already partially absorbed body fluids such as urine, unpleasant odors can quickly occur, caused by the organic components of the urine and the body heat of the wearer. In order to counter this, numerous attempts have been made to achieve a binding of the odor-forming substances by means of corresponding additions to the hygiene article components which are different to the superabsorber, or to cover up this formed odor by means of perfume or the like. The incorporation of such substances in the form of components different to the superabsorber often has a negative effect on the performance of these hygiene articles while they are being worn. Thus, by means of the body fluids, often the odor-inhibiting or -reducing substances are transferred from the components different to the superabsorber into the superabsorber, such as by sponging in, where this has a negative effect on the performance of the superabsorber and thus of the hygiene article in total. Furthermore, it is disadvantageous in this concept, that the greater part of the body fluid given up to the hygiene article is located in the superabsorber anyway, and thus the odor-inhibiting or odor-reducing substances located outside the superabsorber can develop their effect less well.

DE 198 25 486 and DE 199 39 662 A1 disclose the combination of superabsorbers with cyclodextrin for odor-reduction. It can be seen from this otherwise highly promising approach, however, that the cyclodextrin only shows its odor-inhibiting effect in the superabsorber under particular conditions, namely if it is assured that the cyclodextrin is not separated again from the superabsorber. It is here preferred that the cyclodextrin is at least incorporated into the surface of the superabsorber article, in that cyclodextrin and/or cyclodextrin derivatives are covalently and/or ionically bound and/or incorporated therein.

Superabsorbers are further known from DE 103 34 271, which can comprise a plurality of odor binders homogeneously in the agglomerate. This document, which discloses an excellent solution for the use of superabsorber fine particles, does not, however, make available a superabsorber with odor-binding properties which is particularly suitable for application in hygiene articles. Besides an efficient and effective use of the odor binder, the superabsorber properties, which are influenced by the odor binder, are still in need of improvement.

In general, the present invention had the object of reducing or even overcoming the disadvantages arising from the prior art.

An object according to the invention consisted in providing a superabsorbing composition, which, on the one hand, has good odor-binding properties. It should, on the other hand, also be achieved that the performance of the hygiene article which comprises this odor-binding superabsorber composition is substantially as good as or even better than the performance of the hygiene article with a superabsorber which does not comprise the odor-binder as the odor-binding superabsorbing composition.

Furthermore, an object according to the invention consisted in providing a process for obtaining such a superabsorbing composition.

In addition, an object according to the invention consisted in providing a hygiene article which, in addition to good odor-binding properties, also has a good performance. Of particular significance in this context is the absorption rate of the hygiene article upon multiple wetting and the liquid distribution. Both properties are of significance in connection with a good wearing comfort of the hygiene article in addition to the odor reduction.

In addition, the present invention had the object of providing superabsorbing odor-binding substances, which can generally be incorporated into composites or also as composite or which can as such find application in chemical products or components thereof.

A contribution to the solution of the inventive objects is made by the subject matters outlined in the main and sub-claims, whereby the sub-claims represent preferred embodiments.

SUMMARY

The invention thus relates in one variant to an odor-absorbing superabsorbing composition, comprising
i. A water-absorbing polymer structure,
ii. an odor-binder comprising as components
   b1. an amino acid; or
   b2. a compound of general formula I

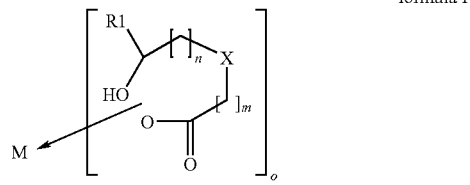

formula I with
R1 as a $C_1$ to $C_{20}$, or a $C_1$-$C_{15}$, or a $C_3$-$C_{10}$ hydrocarbon;
X as not present (in this case there is a direct carbon-carbon bond between the carbon in [ ]$_n$ and the carbon in [ ]$_m$) or a double bond system, in case of at least 2 double bonds, or a conjugated double bond system, comprising in a range from 1 to 5, or from 1 to 3 double bonds, or only one double bond;
M as a charged or uncharged metal;
m in a range from 1 to about 15, or from about 3 to about 12, or from about 5 to about 9;
n in a range from 1 to about 5, or from 1 to about 3, or 1;
o in a range from 1 to about 4, or from 1 to about 3, or from 1 to 2 or 2.

It can be seen from the depiction of formula I that the charged or uncharged, metal M is coordinated at an oxygen of the carboxyl group or at an oxygen of the OH group or both. The part of formula I enclosed in [ ]$_o$ is present as anion, which compensates at least a part of the charge of the metal present as cation. The variables m, n and o form regions in which all conceivable numbers are included, whereby the numbers may be whole, natural numbers.

All hydrocarbons known to the skilled person and suitable may be considered for the residue R1. Hereunder fall aliphatic, double bond-comprising, or aromatic hydrocarbons or acryloalkyls. Aliphatic or double bond-comprising hydrocarbons may be cyclic, branched or unbranched.

In a further variant of the superabsorbing composition according to the invention, the odor binder may be comprised in an amount in a range from 0.01 to about 20 wt. %, or in a range from 0.1 to about 10 wt. %, or in a range from 1 to about 7 wt. %, respectively based on the water-absorbing polymer structure.

It corresponds to another variant of the superabsorbing composition that the odor-binder comprises the components b1 and b2 at the same time. In this case, the superabsorbing composition may comprise component b1 in an amount in a range from about 0.001 to about 20 wt. %, or in a range from about 0.1 to about 10 wt. %, or in a range from about 1 to about 7 wt. %, respectively based on the water-absorbing polymer structure. In addition, it corresponds to a variant of the superabsorbing composition according to the invention, in which the component b2 is comprised in the superabsorbing composition according to the invention in an amount in a range from about 0.01 to about 20 wt. %, or in a range from about 0.1 to about 10 wt. %, or in a range from about 1 to about 7 wt. %, respectively based on the water-absorbing polymer structure.

In another variant of the superabsorbing composition according to the invention, the metal M may be selected from the group consisting of monovalent, divalent and trivalent metals, wherein divalent have a better reactivity with the mostly nucleophilic odor molecules. From a chemical viewpoint, these can be Ti, V, Mn, Fe, Co, Ni, Zn, Cd, and Hg. However, for toxicological and ecological reasons, Zn may be used for the use of component b2 in a superabsorbing composition or in hygiene articles.

In the superabsorbing composition according to the invention, component b2 may be an unbranched or branched, unsaturated or saturated, singly or plurally hydroxylated fatty acid with at least about 16 and often up to about 100 carbon atoms, or salt thereof as well as of any mixtures of at least two of these fatty acids or their salts. In particular, zinc salts may be used in combinations with zinc salts of the resin acids, in particular abietic acid, or with zinc salts of other saturated or unsaturated, hydroxylated fatty acids with about 16 carbon atoms and up to about 100 carbon atoms, whereby in particular, zinc salts of fatty acids, such as ricinoleic acid, whose production is described in DE-B 17 92 074, alone or in combination with other active substances and/or known odor absorbers, may be used. Component b1 may be a zinc salt of ricinoleic acid.

As amino acid in component b1, in principle any amino acid appearing reasonable to the skilled person in connection with the present invention may be considered. Under the term amino acids presently fall both the respective amino acids, their derivatives, as well as the salts of these amino acids and/or of these derivatives. In an embodiment according to the invention, two different amino acids may be combined in component b1. Among the amino acids, in particular, α-, β- or γ-amino acids may be used. Thus, for example, two α-amino acids may be combined. Among the α-amino acids, in particular the amino acids methionine, arginine, and cysteine may be used. However, in addition to cysteine, or also by itself, the amino acid arginine as such may be used, or at least represent the amino acid with the highest concentration in the odor binder. This is particularly true for the case that the components b1 and b2 are used at the same time. With odor binders comprising amino acids, care should be taken that the amino acids comprised therein do not loose their odor-binding effect through a too high thermal load during the production or further processing of the odor-absorbing superabsorbing composition according to the invention.

According to another embodiment of the superabsorbing composition further comprises iii) a polymeric binder which is different to the water-absorbing polymer structure. As polymeric binder, in principle, all polymeric binders known to the skilled person for the purpose of fixing odor-binders, and appearing suitable, may be considered. Among these, thermoplastic polymers may be used. In this context, reference is made to the thermoplastic polymers described in WO 2005/011860. Polymeric binders of this type may have a molecular weight determined by GPC (Gel Permeation Chromatography) and absolutely detectable by means of light scattering, in a range from about 1000 to about 100,000, or from about 2000 to about 50,000, or from about 3000 to about 15,000 g/mol. Polymeric binders of this type may comprise two or more OH groups. Examples of suitable polymeric binders are polyalkylene glycols, such as polyethylene glycol, polypropylene glycol, whereby polyethylene glycol, and a polyethylene glycol with a molecular weight in a range from about 5000 to about 15,000 g/mol. The molecular weights given here relate respectively to the weight average of the molecular weight.

Polymer structures according to the invention may include fibers, foams or particles, whereby fibers, and particles.

Numerous other embodiments, features, and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to shall be considered to support claims to any of the following ranges: 1-5; 1-4; 1-3; 1-2; 2-5; 2-4; 2-3; 3-5; 3-4; and 4-5.

FIGURES

The foregoing and other features, aspects, and advantages of the present invention will become better understood with regard to the following description, appended claims, and accompanying drawings where:

DETAILED DESCRIPTION

Figure 1:
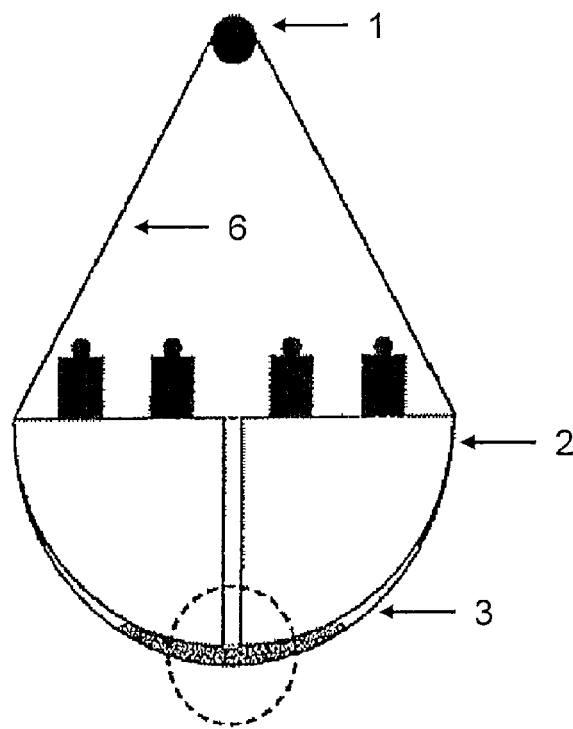
FIG. 1 is a side section through the measurement device determination of acquisition time and liquid distribution of the core.

In an embodiment of the present invention, it is preferred that in the composition according to the invention the water-absorbing polymer structure is based on less than about 40 wt. %, or less than about 30 wt. %, or less than about 20 wt. %, or less than about 10 wt. %, respectively based on the water-absorbing polymer structure, of superabsorber fine particles with a particle size of less than about 150 μm, determined according to ERT 420.1-99. The superabsorber fine particles may have a same or also a different chemical composition compared to the water-absorbing polymer structures. In general, the superabsorber fine particles and the water-absorbing polymer structure contained in the composition according to the present invention are similar in their chemical composition and differ principally in their particle size.

According to a further aspect of the composition of this invention, the water-absorbing polymer structure may comprise at least about 60 wt. %, or at least about 70 wt. %, or at least about 80 wt. %, or at least about 90 wt. %, respectively based on the water-absorbing polymer structure, particles with a particle size in a range from about 150 to about 850 μm as determined according to ERT 420.1-99.

In another embodiment of the composition according to the invention, it is based to less than about 20 wt. %, or less than about 10 wt. %, or less than about 5 wt. %, based on the composition, of a cross-linkable, non-cross-linked polymer. In connection with the cross-linkable, non-crosslinked polymer, reference is made as part of the present text to DE 103 34 271 A1 and there in particular to the details only in paragraphs [0063] to [0082] which are incorporated by reference as they relate to the present invention.

Preferred polymer fibers according to the invention are dimensioned such that they can be incorporated in or as yarns for textiles and also directly in textiles. According to the invention, the polymer structures present as polymer fibers may have a length in a range from about 1 to about 500 mm, or from about 2 to about 500 mm, or from about 5 to about 100 mm, and a diameter in a range from about 1 to about 200 denier, or from about 3 to about 100 denier, or from about 5 to about 60 denier.

Polymer particles according to the invention may be dimensioned such that they have an average particle size according to ERT 420.2-02 in a range from about 10 to about 3000 μm, or from about 20 to about 2000 μm, or from about 150 to about 850 μm. The portion of polymer particles with a particle size in a range from 300 to 600 μm may be at least about 30 wt. %, or at least about 40 wt. %, or at least about 50 wt. %, based on the total weight of the post-crosslinked, water-absorbing polymer particles.

The water-absorbing polymer structures according to this invention may be based on (α1) from about 20 to about 99.999 wt %, or from about 55 to about 98.99 wt %, or from about 70 to about 98.79 wt % polymerized, ethylenically unsaturated, acid groups-carrying monomers or salts thereof or polymerized, ethylenically unsaturated monomers comprising a protonated or quaternated nitrogen, or mixtures thereof, whereby mixtures comprising at least ethylenically unsaturated, acid groups-comprising monomers, such as acrylic acid, (α2) from 0 to about 80 wt %, or from 0 to about 44.99 wt. %, or from about 0.1 to about 44.89 wt % of polymerizable, monoethylenically unsaturated monomers which are co-polymerizable with (α1), (α3) from about 0.001 to about 5 wt %, or from about 0.01 to about 3 wt %, or from about 0.01 to about 2.5 wt % of one or more crosslinkers, (α4) from 0 to about 5 wt %, or from about 0.001 to about 2.5 wt %, or from about 0.01 to about 1 wt. % of the metal salt, (α5) from 0 to about 5 wt %, or from about 0.01 to about 2.5 wt %, or from about 0.1 to about 1 wt. % of the oxide of the metal, α6) from 0 to about 30 wt %, or from 0 to about 5 wt %, or from about 0.1 to about 5 wt % of a water-soluble polymer, (α7) from 0 to about 20 wt %, or from about 2.5 to about 15 wt %, or from about 3 to about 10 wt % water, and (α8) from 0 to about 20 wt. %, or from 0 to about 10 wt %, or from about 0.1 to about 8 wt % of one or more additives, whereby the sum of the weight amounts (α1) to (α8) is 100 wt %.

The monoethylenically unsaturated, acid groups-comprising monomers (α1) may be partially or fully neutralized. The monoethylenically unsaturated, acid groups-comprising monomers may be neutralized to at least about 25 mol %, or to at least about 50 mol %, or from about 50 to about 80 mol %. In this context, reference is made to DE 195 29 348 A1, whose disclosure limited to neutralization of the monoethylenically unsaturated, acid groups-comprising monomers is hereby introduced as reference. The neutralization may also occur partially or fully after the polymerization. Furthermore, the neutralization may occur with alkali metal hydroxides, alkaline earth metal hydroxides, ammonia as well as carbonates and bicarbonates. In addition, any further base which forms a water-soluble salt with the acid is conceivable. A mix neutralization with different bases is also conceivable. Neutralization with ammonia and alkali metal hydroxides is may be used, with sodium hydroxide and with ammonia may also be used.

Furthermore, the free acid groups may dominate in a polymer, such that this polymer has a pH value lying in the acid range. This acidic water-absorbing polymer may be at least partially neutralized by a polymer with free basic groups such as amine groups, which is basic compared to the acidic polymer. These polymers are described in the literature as "Mixed-Bed Ion-Exchange Absorbent Polymers" (MBIEA polymers) and are disclosed inter alia in WO 99/34843 A1. Generally, MBIEA polymers represent a composition which comprise, on the one hand, basic polymers, which are capable of exchanging anions, and, on the other hand, a polymer which is acidic compared to the basic polymer, and which is capable of exchanging cations. The basic polymer comprises basic groups and is typically obtained by polymerization of monomers which may carry basic groups or groups that may be converted into basic groups. These monomers are, above all, such monomers which may include comprise primary, secondary or tertiary amines or the corresponding phosphines or at least two of the above functional groups. To these groups of monomers belong in particular ethyleneamine, allylamine, diallylamine, 4-aminobutene, alkyloxycycline, vinylformamide, 5-aminopentene, carbodiimide, formaldacine, melamine and the like, as well as their secondary or tertiary amine derivatives.

Ethylenically unsaturated, acid groups-comprising monomers ($\alpha$1) may be those compounds that are mentioned as ethylenically unsaturated, acid groups-comprising monomers ($\alpha$1) in WO 2004/037903 A2, which, only to the extent of disclosure of Ethylenically unsaturated, acid groups-comprising monomers is hereby introduced as reference and thus forms part of the disclosure. Ethylenically unsaturated, acid groups-comprising monomers ($\alpha$1) include acrylic acid and methacrylic acid.

According to an embodiment of the present invention, water-absorbing polymer structures are used in which the monoethylenically unsaturated monomers ($\alpha$2) which are copolymerizable with ($\alpha$1) may be acrylamides, methacrylamides or vinyl amides. (Meth)acrylamides may, in addition to acrylamide and methacrylamide include alkyl-substituted (meth)acrylamides or amino alkyl-substituted derivatives of (meth)acrylamide, such as N-methylol (meth)acrylamide, N,N-dimethylamino(meth)acrylamide, dimethyl(meth)acrylamide or diethyl(meth)acrylamide. Possible vinyl amides are, for example, N-vinylamide, N-vinylformamide, N-vinyllacatamide, N-vinyl-N-methylacatamide, N-vinyl-N-methylformamide, vinylpyrrolidone. Among these monomers, acrylamide may be used.

According to another embodiment of the present invention, water-absorbing polymer structures may be used, in which the monoethylenically unsaturated monomers ($\alpha$2) which are copolymerizable with ($\alpha$1) are water-soluble monomers. In this context, in particular alkoxypolyalkylene oxide (meth) acrylates such as methoxypolyethylene glycol (meth)acrylate may be used.

Furthermore, water-dispersible monomers may be used as monoethylenically unsaturated monomers ($\alpha$2) which are copolymerizable with ($\alpha$1). Water-dispersible monomers may include acrylic acid esters and methacrylic acid esters, such as methyl(meth)acrylate, ethyl(meth)acrylate, propyl(meth)acrylate or butyl(meth)acrylate.

The monoethylenically unsaturated monomers ($\alpha$2) that may be copolymerizable with ($\alpha$1) further comprise methylpolyethylene glycol allylethers, vinyl acetate, styrene, and isobutylene.

Crosslinker ($\alpha$3) compounds may include those mentioned in WO 2004/037903 A2 as crosslinker ($\alpha$3). Among these crosslinkers, water-soluble crosslinkers may be used including N,N'-methylenebisacrylamide, polyethylene glycol di(meth)acrylates, triallylmethylammonium chloride, tetraallylammonium chloride as well as allylnonaethylene glycol acrylate prepared with 9 mol ethylene oxide per mol acrylic acid.

All metal salt ($\alpha$4), known to the skilled person, which can be water-insoluble or water-soluble, may be used, whereby, however, water-soluble metal salts may be used. By "water-soluble" is understood to include metal salts of which, at a temperature of 25° C., at least about 1 g, or at least about 10 g, or at least about 100 g, or at least about 500 g may be resoluble in one liter of distilled water.

Water-soluble metal salts may include sulfates, sulfites, sulfides, chlorides, bromides, iodides, nitrates, nitrites, phosphates, phosphites, carbonates, hydrogencarbonates, hydroxides, acetates, lactates and oxalates.

The metal cation of the metal salt may be a monovalent, divalent or a trivalent metal cation. Metal cations may include $Na^+$, $K^+$, $Li^+$, $Mg^{2+}$, $Ca^{2+}$, $Fe^{2+}$, $Fe^{3+}$, $Ag^+$, $Cu^+$, $Cu^{2+}$, $Zn^{2+}$, as well as $Al^{3+}$.

The following metal salts may be used as surface treatment agent in the water-absorbing polymer structures according to the invention: $AlCl_3 \cdot 6H_2O$, $NaAl(SO_4)_2 \cdot 12\ H_2O$, $Al(NO_3)_3 \cdot 9H_2O$, $KAl(SO_4)_2 \cdot 12H_2O$ or $Al_2(SO_4)_3 \cdot 14\text{-}18\ H_2O$ as well as the corresponding anhydrous salts, $Na_2SO_4$ or hydrates thereof, $MgSO_4 \cdot 10H_2O$ or anhydrous magnesium sulphate.

As water-absorbing polymer structure, polymers may be used according to the invention that have been obtained by a process comprising the process steps:

a) radical polymerization of acid groups-carrying, ethylenically unsaturated, optionally partially neutralized monomers in the presence of a crosslinker to form a hydrogel;
b) optionally, comminution of the hydrogel;
c) drying of the optionally comminuted hydrogel to obtain water-absorbing polymer structures;
d) optionally, milling of the thus-obtained absorbent polymer structure and sieving to a desired particle size fraction;
e) optionally, further surface modification of the thus-obtained water-absorbing polymer structures.

Suitable mixing aggregates for surface modification and also for application of the odor binder or at least of one of its components, may include the Patterson-Kelly mixer, DRAIS turbulence mixer, Lödige mixer, Ruberg mixer, screw mixer, plate mixer, and fluidized bed mixer, as well as continuously operating vertical mixers, in which the polymer structure is mixed at high frequency by means of rotating knives (Schugi mixer).

The radical polymerization occurring in process step a) may occur in aqueous solution, whereby this aqueous solution comprises, in addition to water as solvent, ($\alpha$1) the ethylenically unsaturated, acid groups-carrying monomers or salts thereof, whereby acrylic acid is particularly preferred as acid groups-carrying monomer,
($\alpha$2) optionally, monoethylenically unsaturated monomers which are co-polymerizable with ($\alpha$1),
($\alpha$3) the crosslinker,
($\alpha$6) optionally, a water-soluble polymer, as well as
($\alpha$8) optionally, one or more additives.

As ethylenically unsaturated, acid groups-carrying monomers ($\alpha$1), as monoethylenically unsaturated monomers ($\alpha$2) which are copolymerizable with ($\alpha$1), as crosslinker ($\alpha$3), as water-soluble polymers ($\alpha$6) and as additive ($\alpha$8) may include those compounds which have already been mentioned in connection with the polymer structures according to the invention as ethylenically unsaturated, acid groups-carrying monomers ($\alpha$1), as monoethylenically unsaturated monomers (α2) which are copolymerizable with (α1), as crosslinkers (α3), as water-soluble polymers (α6) and as additive (α8).

The water-absorbing polymer structures may be produced from the above-mentioned monomers, co-monomers, crosslinkers, water-soluble polymers and additives by various polymerization methods. For example, in this context, mass polymerization, which preferably occurs in kneading reactors such as extruders, solution polymerization, spray polymerization, inverse emulsion polymerization, and inverse suspension polymerization should be used. Solution polymerization may be carried out in water as solvent. Solution polymerization can occur continuously, by means of polymerization on a belt which further conveys the reaction mixture, as disclosed in DE 35 44 770 A1, or discontinuously. A broad spectrum of variation possibilities with respect to the reaction conditions such as temperatures, type and amount of initiators as well as of the reaction solution can be found in the prior art. Typical processes are described in the following patent documents: U.S. Pat. No. 4,286,082, DE 27 06 135, U.S. Pat. No. 4,076,663, DE 35 03 458, DE 35 44 770, DE 40 20 780, DE 42 44 548, DE 43 23 001, DE 43 33 056, DE 44 18 818.

The polymerization may be started by means of initiator. As initiator for initiation of the polymerization, all initiators which form radicals under the polymerization conditions may be used, which are generally used in the production of superabsorbent polymers. An initiation of the polymerization by the effect of electron beams on the polymerizable aqueous solution is also possible. The polymerization may, however, also be started in the absence of initiators of the above-mentioned type, by the effect of energetic radiation in the presence of photo-initiators. Polymerization initiators may be comprised dissolved or dispersed in a solution of monomers according to the invention. As initiators, all compounds which decompose to radicals and which are known to the skilled person are considered. Hereunder fall, in particular, those initiators which are already mentioned as possible initiators in WO 2004/037903 A2.

In the production of the water-absorbing polymer structures, a redox system including hydrogen peroxide, sodium peroxodisulfate and ascorbic acid may be used.

Inverse suspension polymerization and emulsion polymerization may also be used for production of the polymer structures. According to these processes, an aqueous, partially neutralized solution of the monomers (α1) and (α2), optionally comprising water-soluble polymers and additives, is dispersed, with assistance from protecting colloids and/or emulsifiers, in a hydrophobic organic solvent, and the polymerization started by radical initiators. The crosslinkers may either be dissolved in the monomer solution and are dosed together with this, or are added separately, and optionally during the polymerization. Optionally, the addition of a water-soluble polymer (α6) as graft basis occurs by means of the monomer solution or by direct addition into the oil phase. The water is then removed azeotropically from the mixture and the polymer filtered away.

Furthermore, both with solution polymerization as well as with inverse suspension and emulsion polymerization, the crosslinking may occur by polymerization in of the polyfunctional crosslinker dissolved in the monomer solution and/or by reaction of suitable crosslinkers with functional groups of the polymer during the polymerization steps. The processes are described, for example, in the publications U.S. Pat. No. 4,340,706, DE 37 13 601, DE 28 40 010 and WO 96/05234 A1.

The hydrogels obtained in the solution polymerization or the inverse suspension and emulsion polymerization in process step a) are dried in process step c).

In particular in the case of solution polymerization, the hydrogels, before the drying, are first comminuted in an additional process step b). This comminution occurs by means of comminuting devices known to the skilled person, such as a chopping knife (see DE 195 18 645 C1) or, for example, a meat grinder, which can be connected after the chopping knife.

Drying of the hydrogel may occur in suitable dryers or ovens. By way of example, rotary ovens, fluidized bed dryers, plate dryers, paddle dryers or infrared dryers are mentioned. The drying of the hydrogel in process step c) may occur to a water content of from about 0.5 to about 25 wt. %, or from 1 to about 10 wt %, whereby the drying temperatures generally lie in a range from about 100 to about 200° C.

The dried, water-absorbing polymer structures obtained in process step c) may, in particular if they have been obtained by solution polymerization, be further milled and sieved to the above-mentioned desired particle sizes in a further process step d). The milling of the dried, water-absorbing polymer structures may occur in suitable mechanical comminution devices, such as, for example, a ball mill.

Following the drying of the hydrogels and after the optionally carried out further confectioning of the dried, water-absorbing polymer structures, these may be modified in the surface region in a further process step e). This may occur by means of a metal salt or with the combination of the metal salt and the oxide of a metal or with another modification agent or by means of another modification agent, whereby the above materials can be applied as aqueous solution or as solid. The confectioning can occur both on the water-absorbing polymer structure as well as on the superabsorbing composition already comprising the odor binder.

Surface post-crosslinking is mentioned here as a modification measure, in which the dried polymer structure or the not yet dried, but already comminuted hydrogel is brought into contact with a organic, chemical surface post-crosslinker. In particular if the post-crosslinker is not liquid under the post-crosslinking conditions, it is brought into contact with the polymer particles or with the hydrogel by means of a solvent. As solvent, preferably water, organic solvents which are miscible with water such as methanol, ethanol, 1-propanol, 2-propanol or 1-butanol, or mixtures of at least two of these solvents may be used. Furthermore, the post-crosslinker may be comprised in the solvent or solvent mix in an amount in a range from about 5 to about 75 wt. %, or from about 10 to about 50 wt. %, or from about 15 to about 40 wt %, based on the total weight of the solvent or solvent mix.

The bringing into contact of the polymer structure or of the comminuted hydrogel with the solvent or solvent mixture comprising the post-crosslinker preferably may occur in the process according to the invention by good mixing of the solvent or solvent mixture with the polymer structure.

Suitable mixing aggregates for mixing may include, e.g. the Patterson-Kelley mixer, DRAIS turbulence mixer, Lödige mixer, Ruberg mixer, screw mixer, plate mixer, and fluidized bed mixer, as well as continuously operating vertical mixers, in which the polymer structure may be mixed at high frequency by means of rotating knives (Schugi mixer).

In the process according to the invention, in the post-crosslinking, the polymer structure may be brought into contact with at most about 20 wt %, or with at most about 15 wt %, or with at most about 10 wt %, or with at most 5 wt % of solvent, such as water.

With polymer structures in the form of approximately spherical particles, it may be that the bringing into contact may occur in such a way that only the outer region, not, however, the inner region of the particulate polymer structures are brought into contact with the solvent or solvent mixture and thus with the post-crosslinker.

As post-crosslinkers that may be used in the process according to the invention, may include compounds that comprise at least two functional groups which can react with functional groups of a polymer structure in a condensation reaction (=condensation crosslinker), in an addition reaction or in a ring opening reaction. As post-crosslinker, in the process according to the invention are preferred those which were mentioned in WO 2004/037903 A2 as crosslinkers of crosslinker class II.

These compounds may include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one as well as 1,3-dioxolan-2-one.

After the polymer structures or the hydrogels have been brought into contact with the post-crosslinker or with the fluid comprising the post-crosslinker, they are heated to a temperature in a range from about 50 to about 300° C., or from about 75 to about 275° C., or from about 150 to about 250° C., so that the outer region of the polymer structures is more strongly crosslinked compared to the inner region (i.e., post-crosslinking). The duration of the heat treatment is limited by the risk that the desired property profile of the polymer structures will be destroyed as a result of the effect of heat.

In an embodiment of the composition according to the invention the polymer structure comprises
an inner region, and
an outer region surrounding the inner region,
whereby the outer region has a higher degree of crosslinking than the inner region. In this context, it is preferred that the concentration of the odor binder in or on the outer region is higher than the concentration of the odor binder in the inner region. In this way a type of core-shell morphology forms in the composition according to the invention, both with respect to the crosslinking as well as with respect to the odor binder concentration. This is in particular the case if the odor binder is situated on the surface of the water-absorbing polymer structure, optionally with only little penetration depth (mostly less than 2% of the diameter of the water-absorbing polymer structure) into the water-absorbing polymer structure. This can be achieved in particular, in that the odor binder is added at the end of or after the surface crosslinking.

In another embodiment of the composition according to the invention, the polymer structure comprises
an inner region, and
an outer region surrounding the inner region,
whereby the concentration of the odor binder in or on the outer region is higher than the concentration of the odor binder in the inner region.

In a further embodiment of the process according to the invention, the confectioning of the water-absorbing polymer structure or of the superabsorbing composition occurs by bringing into contact with metal salts and/or with a combination of the metal salt and the oxide of a metal and/or modification agents before the water-absorbing polymer structure has been brought into contact with a post-crosslinker mentioned in WO 2004/037903 A2 as crosslinker of crosslinker class II.

In addition, the invention relates to a process for production of a superabsorbing composition, comprising the process steps:
I. provision of a water-absorbing polymer structure, which can preferably be obtained in the above-described way;
II. bringing into contact of the surface of the water-absorbing polymer structure with an odor binder comprising a component B1 or a component B2.

In connection with the components B1 and B2, reference is made to the above details concerning components b1 and b2, whereby the details in this context also apply to components B1 and B2.

The bringing into contact can generally occur by any method appearing suitable to the skilled person. According to one embodiment of the process according to the invention, the bringing into contact occurs by mixing of water-absorbing polymer structures with the odor binder. In this context, it is preferred that both the water-absorbing polymer structure and the odor binder or binders are present in powder form and thus as particles. It has further proven advantageous, that in the mixing together of the water-absorbing polymer structure present as powder and the odor binder, which is likewise present as powder, the average particle sizes according to ERT 420.2-02 are different. In this case, the water-absorbing polymer structure should have a larger particle size than the odor binder. The average particle sizes according to ERT 420.2-02, of the water-absorbing polymer structure and the odor binder differ by at least a factor of 2, or by at least a factor of 5, or by at least a factor of 10.

In an embodiment of the process according to the invention, the water-absorbing polymer structure may comprise less than about 40 wt %, or less than about 30 wt %, or less than about 20 wt %, or less than about 10 wt %, respectively based on the water-absorbing polymer structure, superabsorber fine particles with a particle size of less than about 150 µm, determined according to ERT 420.1-99.

In another embodiment of the process according to the invention, the water-absorbing polymer structure may comprise at least about 60 wt %, or at least about 70 wt %, or at least about 80 wt %, or at least about 90 wt %, respectively based on the water-absorbing polymer structure, particles having a particle size in a range from about 150 to about 850 µm, determined according to ERT 420.1-99.

In another embodiment of the process according to the invention, it is possible that less than about 20 wt %, or less than about 10 wt %, or less than about 5 wt %, respectively based on the composition, of a cross-linkable, non-crosslinked polymer is used as a binder.

In another embodiment of the process according to the invention, the odor binder may be applied, together with a fluid, such as water, isopropanol, ethanol, or acetone, to the water-absorbing polymer structure. The amount of liquid used here may lie in a range from about 0.1 to about 20 wt %, or in a range from about 1 to about 15 wt %, or in a range from about 3 to about 17 wt %, respectively based on the weight of the dry water-absorbing polymer structure. It is further helpful in some cases to use a solvent or solvent mixture when mixing the odor binder with the water-absorbing polymer structure. In this context, the above-described solvents or solvent mixtures, and the there described concentrations are likewise preferred. Care should be taken in this case to use as little solvent or solvent mixture as possible, since this must be removed again, optionally by drying.

The bringing into contact of the odor binder may, on the one hand, occur already during the production of the water-absorbing polymer structure, in that the odor binder, in particular the odor binder B2, especially if it comprises a double bond, is already mixed with the reagents used for radical polymerization of the water-absorbing polymer structure. In this way, it can be achieved that the odor binder and in particular component B2, especially if it comprises a double bond, is incorporated as homogeneously as possible and as strongly bound as possible with the water-absorbing polymer structure.

In another embodiment of the process according to the invention, the bringing into contact of the odor binder with the water-absorbing polymer structure occurs, whereby the water-absorbing polymer structure is present as hydrogel. By hydrogel is generally understood a water-absorbing polymer structure which is swollen with water or with an aqueous solution. Hydrogels for processing in the context of the process according to the invention may comprise a water or aqueous fluid content of at least about 10 wt %, or in a range from about 20 to about 200 wt % of the fluid, respectively based on the dry weight of the water-absorbing polymer structure. Also in connection with the application of the odor binder to a water-absorbing polymer structure present as hydrogel, it is preferred that the hydrogel is present as granulate, so that the odor binder particles, which, in comparison to the size of these granulate particles are substantially smaller, and which can likewise be present as dispersion or even dissolved in a fluid, can be distributed as uniformly as possible on the surface of the hydrogel granulate. In a further embodiment of the process according to the invention, in which the water-absorbing polymer structure is present as hydrogel at the bringing into contact with the odor binder, it is preferred also to use other substances used for post-treatment of the hydrogel, whereby the above-described post-crosslinkers are particularly preferred. In the case that post-crosslinkers are applied to the hydrogel additionally to the odor binders, the—likewise above described—thermal treatment for post-crosslinking is carried out after the bringing into contact.

In the case of the bringing into contact of the water-absorbing polymer structure with an amino acid, in particular with cysteine, this may occur at temperatures of below about 150° C., or below about 100° C., or below about 80° C. A procedure which is particularly gentle on the odor binding properties of the odor binder comprising an amino acid, in particular cysteine, provides, during the bringing into contact and the, in the case of the use of a mostly aqueous amino acid-comprising solution, then following drying step and optionally further following processing steps, that at least the bringing into contact, preferably at least the bringing into contact and the drying, may occur at temperatures in a range from about 15 to about 80° C., or from about 20 to about 75° C., or in a range from about 25 to about 70° C. It is further possible, to support the drying, to apply a reduced pressure, which generally lies in a range from normal pressure to about 10 Torr.

According to another embodiment of the process according to the invention, for the bringing into contact with the odor binder, a water-absorbing polymer structure with a water content of less than about 10 wt %, or less than about 7 wt %, or less than about 6 wt %, respectively based on the dry polymer structure, is used. The water content may be determined according to the EDANA method ERT 430.1-99. The water-absorbing polymer structure with the low water content can be, according to an embodiment of the process according to the invention, a not yet post-crosslinked water-absorbing polymer structure and, according to another embodiment of the process according to the invention, an already post-crosslinked water-absorbing polymer structure.

For the case that the odor binder is brought into contact with the water-absorbing polymer structure with the aid of a liquid, to at least partially remove the liquid used from the thus-obtained superabsorbing composition, by drying. When selecting the condition for this drying process, care should be taken that the odor-binder is not limited in its odor-binding activity. Generally, the drying temperatures may lie in a range from about 30 to about 200° C., or in a range from about 50 to about 150° C., or in a range from about 70 to about 120° C. The drying process may be carried out for at least about five minutes, or at least about ten minutes, or in a range from about 15 to about 180 minutes. For a suitable selection of the drying conditions, care should likewise be taken for the case in which the odor binder is brought into contact, together with a post-crosslinker, with the water-absorbing polymer structure and the post-crosslinking should occur after the bringing into contact.

Furthermore, it corresponds to an embodiment of the process according to the invention that the bringing into contact occurs further III in the presence of a polymeric binder. In connection with the polymeric binder III, reference is made to the details concerning the polymeric binder iii, whereby the above details also apply to the polymeric binder III. The polymeric binder is preferably used in the process according to the invention if the odor binder is not applied as liquid but as solid. The application of the polymeric binder can occur both on the water-absorbing polymer structure present as hydrogel, as well as on the dried water-absorbing polymer structure and in particular on the already post-crosslinked water-absorbing polymer structure, respectively together with the odor binder. It corresponds to an embodiment of the process according to the invention that the bringing into contact of the odor binder or of the odor binder with the polymeric binder with a water-absorbing polymer structure occurs, whereby the water-absorbing polymer structure is preferably not present as hydrogel but dry, as described above. In other words, the water-absorbing polymer structure may be surface crosslinked before the bringing into contact. This surface crosslinking not only includes the application of the surface crosslinker but also the surface crosslinking reaction, which generally occurs by thermal treatment.

A further contribution to the solution of the above-described objects is provided by the superabsorbing compositions obtainable by the process according to the invention. The superabsorbing composition according to the invention preferably has as property a retention according to ERT 441-2-02 of at least about 20 g/g, or at least about 25 g/g, or in a range from about 25 to about 50 g/g;

an absorption under a pressure of 0.7 psi of at least about 10 g/g, or at least about 13 g/g, or in a range from about 13 to about 30 g/g.

The superabsorbing compositions according to the invention obtainable by the process according to the invention may comprise the same properties as described above for the superabsorbing compositions. Those values that have been given, in connection with the process according to the invention and the polymer structures according to the invention as well as the superabsorbing compositions, as lower limits of features according to the invention, without upper limits, have upper limits which are 20 times, or times, or 5 times the most preferred value of the lower limit.

A further contribution to the solution of the above-described objects is provided by a composite comprising the water-absorbing polymer structures according to the invention or respectively the surface-treated water-absorbing polymer structures obtainable by the process according to the invention and a substrate. The polymer structures according to the invention and the substrate are strongly bound with each other. As substrate, sheets made from polymers, such as, for example, from polyethylene, polypropylene or polyamide, metals, non-woven materials, fluff, tissues, woven materials, natural or synthetic fibers, or other foams, are preferred. It is further preferred according to the invention that the composite comprises at least one region which comprises the water-absorbing polymer structure according to the invention in an amount in a range from about 15 to 100 wt. %, or about 30 to 100 wt. %, or from about 50 to 99.99 wt. %, or from about 60 to 99.99 wt %, or from about 70 to 99 wt. %, respectively based on the total weight of the relevant region of the composite, whereby this region preferably has a size of at least about $0.01 \text{ cm}^3$, or at least about $0.1 \text{ cm}^3$, or at least about $0.5 \text{ cm}^3$.

In an embodiment of the composite according to the invention, it is a sheet-like composite, as described in WO 02/056812 A1 as "absorbent material". The disclosure of WO 02/056812 A1, in particular concerning and limited to the exact construction of the composite, the basis weight of its components as well as its thickness is hereby introduced as reference and represents a part of the disclosure of the present invention.

A further contribution to the solution of the above-mentioned objects is provided by a process for production of a composite, whereby the superabsorbing composition according to the invention or the surface treated water-absorbing polymer structures obtainable by the process according to the invention and a substrate and optionally an additive are brought into contact with each other. Such substrates are used which have already been mentioned in connection with the composite according to the invention.

A contribution to solving the above-mentioned object is also provided by a composite obtainable by the above-described process, whereby this composite has the same properties as the above-described composite according to the invention.

According to another aspect of the present invention, the composite is formed as a hygiene article core, which, respectively based on the hygiene article core, comprises at least about 30 wt %, or at lest about 50 wt %, or at least about 70 wt % of the water-absorbing composition according to the invention and at least about 1 wt %, or at least about 5 wt %, or at least about 10 wt % of the substrate and optionally yet further common additives and/or adhesives, whereby the sum of the weight percent of the individual components comprised in the hygiene article core is 100 wt. %. As substrate in connection with the hygiene article core are preferred in particular materials which serve to fix the superabsorbing composition according to the invention, which is mostly present as particles. This can here be fibers or interlaced materials or woven materials as well as nets. It is further possible that the superabsorbing composition which is present, for example, as powder and thus in particle form, is bound with the substrate by means of an adhesive such as a glue. Likewise, it corresponds to an embodiment that the substrate is designed such that the superabsorbing composition is received in a recess of the substrate. Common additives which can likewise be incorporated in the hygiene article core are, for example, materials, cosmetic materials which increase the skin tolerance, disinfection agents, antimicrobial substances and the like.

In a further aspect, the present invention relates to hygiene articles comprising a liquid-permeable top sheet, a liquid-impermeable bottom sheet and a composite according to the invention arranged between the top sheet and the bottom sheet. As hygiene article, both feminine hygiene articles, adult incontinence products as well as diapers for infants, babies and small children come into consideration. It is preferred that the hygiene article comprises an above-described hygiene article core. As liquid-permeable top sheet, in principle all woven materials, laid materials and interlaced materials known and appearing suitable to the skilled person hereof, which mostly consist of celluloses or cellulose derivatives, which are optionally fortified with artificial materials such as polypropylene or polyethylene, come into consideration. Also used as liquid-impermeable bottom sheet are the non-woven materials commonly known to the skilled person and mostly likewise consisting of a cellulose or cellulose derivative, laid material, interlaced material, or knitted material, whereby these are generally provided with a plastic sheet, mostly made from polypropylene or polyethylene.

A further contribution to the solution of the above-mentioned object is provided by chemical products comprising the superabsorbing compositions according to the invention or a composite according to the invention. Chemical products include foams, formed bodies, fibers, sheets, films, cables, sealant materials, liquid-absorbing hygiene articles, in particular diapers and sanitary napkins, carriers for plant or fungus growth regulating agents or plant protection active substances, additives for construction materials, packaging materials, or soil additives.

The use of the polymer structures according to the invention or of the composite according to the invention in chemical products, preferably in the above-mentioned chemical products, in particular in hygiene articles such as diapers or sanitary napkins, as well as the use of the superabsorber particles as carriers for plant or fungus growth regulating agents or plant protection active substances also provides a contribution to the solution of the above-mentioned objects. In the use as carrier for plant or fungus growth regulating agents or plant protection active substances, it is preferred that the plant or fungus growth regulating agent or plant protection active substances can be released over a time period controlled by the carrier.

The invention is illustrated by non-limiting examples in the following.

Test Methods

General

Unless other test methods are given in the following, the test methods generally known to the skilled person and commonly appearing are used, whereby in particular test methods of EDANA (European Diaper and Non Woven Association) find application, which are generally given as "ERT methods".

Retention and Absorption

Retention is determined as CRC (Centrifuge Retention Capacity) according to ERT 441.2-02 on the total particle fraction, whereby absorption was for 30 minutes and directly afterwards centrifugation for three minutes. The absorption under pressure was determined as AAP (Absorption Against Pressure) according to ERT 442.2-02 on the total corn fraction.

Determination of the Wicking Index

The determination of the wicking index occurred according to the test process described on page 6, line 36 to page 7, line 26 of EP-A-0 532 002, whereby the total particle fraction was used and, in place of the synthetic urine, a 0.9% aqueous salt solution (prepared from distilled water and NaCl p.a. with a pH value in a range from 5.0 to 8.0) was used.

Odor Binding

The odor binding was determined by means of headspace gas chromatography (GC). In order to determine the decrease in odor substances in the headspace, a sample of superabsorbing composition of 100.0 mg was weighed into a closable pressure vial (10 ml headspace pressure vial Hewlett Packard® part number: 9301-0717) and combined with an aqueous solution of the odorous substance (1 µl of a stock solution of 50 mmol/l furfurylmercaptan in dimethylformamide was added to 25 ml water). After a waiting period of 16 h at room temperature, a tempering of the pressure vial in the oven of the headspace sample dispenser (Hewlett Packard® 7694) was carried out as described more closely below. An injection was then made from the vapor phase of the pressure vial into the GC Hewlett Packard® 5890 A. The separation occurred on an apolar capillary column RTX® 5 (Crossbond® 5% diphenyl-95% dimethyl-polysiloxane, geometry: 60 m·0.53 mm·1.0µ, producer: Restek Corp.), which is attached to an FID detector. In the headspace, the following conditions were maintained: oven temperature: 45° C., loop temperature: 120° C., sTr. line temperature: 120° C., GC cycle time: 12.0 min, vial eq. time: 60.0 min, pressure. time: 0.13 min, loop fill time: 0.02 min, loop eq. time: 0.02 min, injection time: 0.50 min, "shake": off, cartridge pressure: 134 kPa, vial pressure: 152 kPa; temperature program: 170° C. for 0 min, −30° C./min to 110° C. for 2 min, 35° C./min to 250° C. for 2 min; injector: column flow: 13 ml/sec; split (without HS): 0 ml/sec, split (with HS): 150 ml/sec, column pre-pressure: 100 kPa, temperature: 250° C., "purge": on; detector: detector temperature: 250° C., detector range: 0.

For quantification of the decrease, the peak areas of the odorous substance of the sample are compared with a control sample which contains no odor binder.

Acquisition Time and Liquid Distribution

Figure 2:
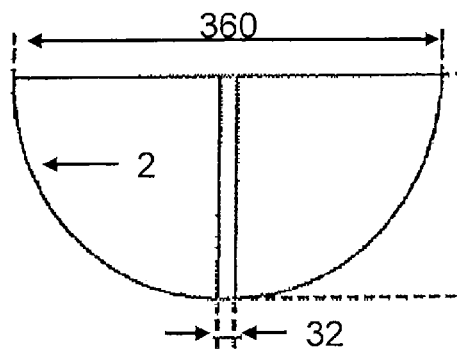
FIG. 2 is a front view of the measurement device from the front view.
Figure 3:
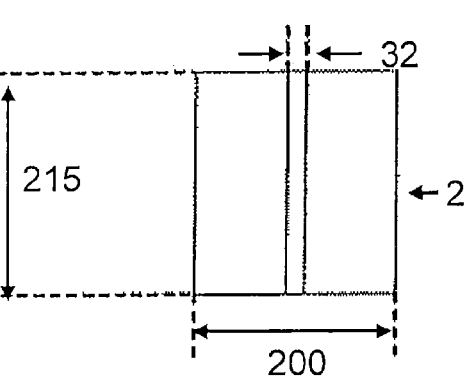
FIG. 3 is a side view of the measurement device.
Figure 4:
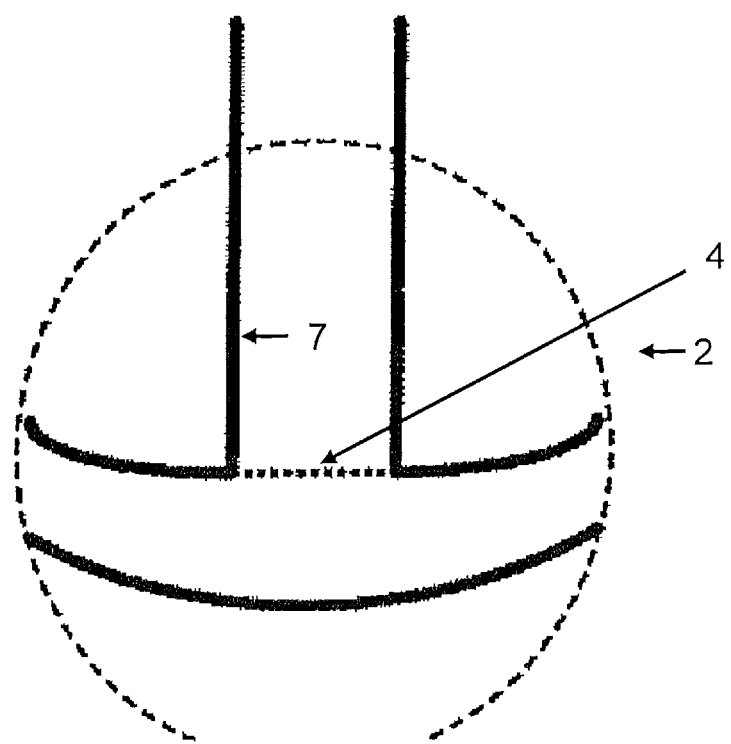
FIG. 4 is a sectional view of FIG. 1.

The measurement device for determination of acquisition time and liquid distribution of the core is shown schematically in FIGS. 1 to 4. FIG. 1 shows a side section through the measurement device, whereby at a mounting 1 formed as a laboratory rod an insert 2 based in principle on a seat of a hygiene article wearer and formed from transparent Plexiglas® is held by means of a 200 mm wide, approximately 1 mm thick, non-elastic and smooth plastic sheet 6. The insert 2 is substantially a semi-circle with a smooth surface, which comprises in its centre a channel 7, which, as depicted in section in FIG. 4, has a sieve 4 at its lower opening. The core 3 is placed with its centre, which is determined by eye, below the lower opening of the channel 7. Then, the insert 2 is charged with the weights provided for the measurements. Through the upper opening of the channel 7, the test liquid is filled into the measurement device. FIGS. 2 and 3 give the dimensions of the measurement device from the front view and the side view, in mm. The core with a size of 300 mm length×120 mm width was weighed, laid in the body shaped test apparatus and charged with 9 kg. Afterwards, 60 g of a 0.9% aqueous salt solution, which was colored with 5 ml/l aniline red stock solution (in 1 l of a 0.9% salt solution, 10.0 g aniline red was added and the pH value of the solution adjusted to 6.0 by addition of 0.3% aqueous NaOH) was added three times, by means of measuring cylinder at time intervals of 20 minutes, through the opening of the test apparatus. By means of a stop watch, the infiltration time from start of addition to complete infiltration of the test liquid can be measured. After each liquid addition follows a waiting period of 20 minutes. The weights are then removed. The distribution of liquid was determined respectively after completion of the above-mentioned 20 minutes. To this end, the spread of the liquid in the length of the core was measured.

EXAMPLES

Example 1

Production of a Non-post-crosslinked Water-absorbing Polymer Structure as Hydrogel—Sample a A monomer solution consisting of 280 g acrylic acid, which was neutralized to 70 mol % with sodium hydroxide solution, 466.8 g water, 1.4 g polyethylene glycol-300-diacrylate and 1.68 g allyloxypolyethylene glycol acrylic acid ester was purged of dissolved oxygen by purging with nitrogen and cooled to the start temperature of 4° C. After reaching the start temperature, the initiator solution (0.3 g sodium peroxydisulfate in 10 g $H_2O$, 0.07 g 30% hydrogen peroxide solution in 1 g $H_2O$ and 0.015 g ascorbic acid in 2 g $H_2O$) added. After the end temperature of about 100° C. was reached, the arising gel was minced, so that a granulate with approximately 1 to 3 mm sized particles was obtained as sample a. The water content was about 50%.

Example 2

Production of a Non-post-crosslinked Water-absorbing Polymer Structure as Powder—Sample b Sample a was dried at 150° C. for 120 minutes. The dried polymer was coarsely broken up, milled and sieved to a powder with a particle size from 150 to 850 µm and a sample b with an average particle size according to ERT 420.2-02 of 520 µm was obtained. The water content determined according to ERT 430.1-99 was 5%.

Example 3

Production of a Post-crosslinked Water-absorbing Polymer Structure as Powder—Sample c)

For post-crosslinking, 100 g of the above-obtained powder of sample b was mixed with vigorous stirring with a solution of 1 g 1,3-dioxalan-2-one, 3 g water and then heated for 30 minutes in an oven which was set to 180° C. The thus-obtained sample c had an average particle size according to ERT 420.2-02 of 525 µm. The water content of sample c determined according to ERT 430.1-99 was 4.5%.

Example 4

Superabsorbing Compositions—Odor Binders on Hydrogel With Post-crosslinking 100 dry weight parts of sample a were provided and combined with the amounts given in table 1 (based on the dry mass parts) of odor binder. The mixture was then homogenized by mincing and dried at 150° C. for 120 minutes. The dried polymer was coarsely broken up, milled and sieved to a powder with a particle size from 150 to 850 µm and a sample b with an average particle size according to ERT 420.2-02 of 515 µm obtained. The water content determined according to ERT 430.1-99 was 5.5%. For post-crosslinking, 100 g of the above-obtained powder was mixed with vigorous stirring with a solution of 1 g 1,3-dioxalan-2-one, 3 g water and then heated for 30 minutes in an oven which was set to 180° C. The thus-obtained product was analyzed according to the entries in table 1. The Tegosorb® types used are obtainable commercially from Goldschmidt GmbH. The control sample was treated exactly as above without addition of the odor binder.

TABLE 1

| Sample | Odor binder type and amount (dry mass) | CRC [g/g] | AAP (0,7 psi) [g/g] | Odor binding* [%] |
|---|---|---|---|---|
| 4-1 | 1% Tegosorb ® PY88, 1.5% Cysteine | 30.3 | 14.2 | 80 |
| 4-2 | 1.5% Cysteine** | 28.8 | 18.6 | 88 |
| 4-3 | 1% Tegosorb ® A30, 1.5% Cysteine | —*** | —*** | 83 |

*Furfurylmercaptan reduction in the gas phase in comparison with the same control sample not comprising odor binder;
**Cysteine was always used as 15% aqueous solution;
***No measurement.

It can be seen from table 1 that superabsorbing compositions according to the invention are obtained, which, in addition to good absorption properties, have excellent odor binding. In addition, the wicking indices determined according to EP-A-0 532 002 of sample c and sample 4-2 are the same within the measurement precision of this test.

Example 5

Superabsorbing Compositions—Odor Binder on Post-crosslinked Superabsorbing Polymer 100 dry mass parts of sample c were provided and combined with the amounts given in table 2 (based on the dry weight part) of odor binder and homogenized in an MIT mixer type LM1.5/5 of the company Mischtechnik Industrieanlagen GmbH. The results of the analysis are given in table 2.

TABLE 2

| Sample | Odor binder type and amount (dry mass) | CRC [g/g] | AAP (0,7 psi) [g/g] | Odor binding* [%] |
|---|---|---|---|---|
| 5-1 | 2% Tegosorb ® PY88, 1% PEG 10000** | 30.8 | 21 | 24 |
| 5-2 | 1% Tegosorb ® PY88, 1.5% Cysteine | 28.8 | 21.3 | 88 |
| 5-3 | 1.5% Cystein*** | 29.4 | 22.5 | 74 |
| 5-4 | 1% Tegosorb ® A30, 1.5% Cysteine | 27.1 | 20.9 | 83 |

*Furfurylmercaptan reduction in the gas phase in comparison with the control sample (sample c) not comprising odor binder;
**was used as 25% aqueous solution;
***cysteine was always used as 15% aqueous solution;

It can be seen from table 2 that superabsorbing compositions according to the invention are obtained, which, in addition to good absorption properties, also show excellent odor binding. In addition, the wicking indices of sample c (20.8 cm) and sample 5-3 (19.8 cm) are the same within the measurement error of this test.

Example 6

Superabsorbing Compositions—Odor Binder on Post-crosslinked Superabsorbing Polymer 100 dry mass parts of the post-crosslinked superabsorbing polymer FAVOR® SXM 9155 substantially based on lightly crosslinked acrylic acid partially neutralized to about 75 mol %, obtainable commercially from Stockhausen GmbH, were provided and combined with the amounts (based on the dry mass parts) given in table 3 of odor binder and homogenized in the above-designated MIT mixer.

The cores were formed by means of a mixture of 48.6 wt. % of a superabsorbing composition given in table 3 and described above, based on the core, and 48.6 wt. % cellulose fibers Stora Fluff EF semi treated of the company Stora-Enzo AB Sweden, as well as 2.8 wt. % of a bicomponent fiber made from respectively 50 wt. % polypropylene (PP) and polyethylene (PE) with PP core and PE jacket of the company Fibrevision A/S Denmark by means of an Air laid process with a M and J Machine (width 40 cm, operating width 36 cm, operation null settings: belt speed 3 m/min, fluff feed at hammer mill 3.1 m/min, polymer metering 380 g/min, bicomponent fiber in 10 g portions about 1 times/min discharged), whereby the absorbent polymer was inserted homogeneously. Cores with a basis weight of 756 g/m$^2$, a density of 0.2 g/cm$^3$ were used for the tests. The cores had a length of 300 mm and a width of 120 mm. The results of the core analysis are given in tables 3a and 3b.

TABLE 3a

Acquisition time as 6-times determination

| Sample | Odor binder type and amount (dry mass) | 1st Insult | 2nd Insult | 3rd Insult |
|---|---|---|---|---|
| 6-1 | 2% Cysteine* | 62 s/ 10.3 g/10 s | 493 s/ 1.3 g/10 s | 922 s/ 0.7 g/10 s |
| 6-2 | 1% Tegosorb ® A30, 2% Cysteine | 47 s/ 13.1 g/10 s | 324 s/ 1.9 g/10 s | 672 s/ 0.9 g/10 s |
| 6-3 | 2% Tegosorb ® A30 | 55 s/ 11.1 g/10 s | 377 s/ 1.6 g/10 s | 775 s/ 0.8 g/10 s |
| 6-4 | SXM 9155 - control | 79 s/ 10.3 g/10 s | 758 s/ 0.8 g/10 s | 1352 s/ 0.5 g/10 s |

*cysteine was always used as 15% aqueous solution.

It can be seen from table 3a that superabsorbing compositions according to the invention are obtained, which, in addition to an excellent odor binding, also have clearly improved acquisition times compared to the control without odor binder.

TABLE 3b

Liquid distribution as 6-times determination

| Probe | Odor binder type and amount (dry mass) | 1st Insult | 2nd Insult | 3rd Insult |
|---|---|---|---|---|
| 6-1 | 2% Cysteine* | 11.0 cm/ 37% | 14.2 cm/ 47% | 19.5 cm/ 65% |
| 6-2 | 1% Tegosorb ® A30, 2% Cysteine | 12.0 cm/ 40% | 15.8 cm/ 53% | 21.0 cm/ 70% |
| 6-3 | 2% Tegosorb ® A30 | 12.2 cm/ 41% | 16.3 cm/ 54% | 20.7 cm/ 69% |
| 6-4 | SXM 9155 - control | 11.2 cm/ 37% | 13.3 cm/ 44% | 18.5 cm/ 62% |

*cysteine was always used as 15% aqueous solution.

It can be seen from table 3b that superabsorbing compositions according to the invention are obtained, which, in addition to excellent odor binding also have clearly improved liquid distribution compared to the controls which do not comprise any odor binder.

Example 7

Post-crosslinked Water-absorbing Polymer Structure with Odor Binder—Sample e 100 dry mass weights of a sample d (produced as sample c but with a degree of neutralization of 50 mol %) was mixed with 1 dry mass percent Tegosorb® A30 as a) 15% or b) 25% solution, mixed at room temperature in cylindrical glass bottles for 30 minutes on a roller bench with a rolling speed of 80 rpm and dried at room temperature for 24 h. In case a), a powder with a particle size of 150 to 850 μm was sieved and a sample e-a with an average particle size according to ERT 420.2-02 of 517 μm obtained. The water content determined according to ERT 430.1-99 was 7%. In case (b), a powder with a particle size of 150 to 850 μm was sieved and a sample e-b with an average particle size according ERT 420.2-02 of 521 μm obtained. The water content determined according to ERT 430.1-99 was 6.9%.

Example 8

Post-crosslinked Water-absorbing Polymer Structure with Cysteine as Odor Binder—Sample f 100 dry mass weights of the post-crosslinked superabsorbing polymer Favor® SXM 9155, based substantially on lightly crosslinked acrylic acid partially neutralized to about 75%, obtainable commercially from Stockhausen GmbH, was provided and combined with two dry mass parts of cysteine as a 15% aqueous solution as odor binder, and homogenized in the above-described MIT mixer. The mixture was then dried at 30° C. in a water flow pump vacuum, until the water content determined according to ERT 430.1-99 was 6.5%. A powder with a particle size of 150 to 850 μm was sieved and a sample f with an average particle size according to ERT 420.2-02 of 523 μm was obtained.

Example 9

Preparation of a Post-crosslinked Agglomerated Water-absorbing Polymer Structure—Sample g The preparation of sample b was repeated up to the milling and sieving step, on a 5 kg scale. The thus-obtained product was milled in a centrifugal mill of the type ZM100 from the company Retsch and sieved with an analysis sieve machine of the type AS200 control 'g' from the company Retsch to a first fraction F1 with a particle size less than 150 μm and to a second fraction F2 with a particle size of 150 to 850 μm with an average particle size according to ERT 420.2-02 of 521 μm.

To prepare the binder, in a glass reactor flushed with nitrogen, as sample, 208.16 g 50% NaOH, 842.20 g deionized water, 375.00 g acrylic acid were reacted with an initiator system of 1.12 g mercaptoethanol, 0.22 g ascorbic acid in 9.78 g deionized water and 2.92 g 35% hydrogen peroxide, with a post-catalyst of 13.90 g 35% hydrogen peroxide, 2.42 g hydroxyammonium chloride in 7.58 g deionized water and with the 36.70 g of the crosslinker PEG 300. To this end, the sample was purged for 1 h with nitrogen and at 25° C. the initiator components added in the above order, so that after 5 minutes a reaction temperature of 90° C. was reached and maintained for 30 minutes, before the post-catalyst was added and further stirred for 1 h, after which the preparation was cooled to 50° C.

For the agglomeration, a mixture of 200 g consisting of 40 wt. % of fraction F1 and 60 wt. % of fraction F2 was placed in a MIT-mixer type LM1.5/5 from the company Mischtechnik Industrieanlagen GmbH and 25 wt. % (based on the mixture) of a 25% aqueous solution of the above-prepared binder added over 2 minutes via an injection cannula and mixed for 1 minute to an intimate mixture.

The thus-obtained mixture was dried in a circulating air drying cupboard at 180° C. for 30 minutes and milled in a centrifugal mill of the type ZM100 from the company Retsch control 'g' as agglomerate sieved off with an analysis sieve machine type AS200 from the company Retsch to a fraction with a particle size of 150 to 850 μm with an average particle size according to ERT 420.2-02 of 522 μm.

For the post-crosslinking, 100 g of the above-obtained agglomerate was mixed with vigorous stirring with a solution of 1 g 1,3-dioxolan-2-one, 3 g water, and then heated for 30 minutes in an oven regulated at 180° C. The thus-obtained sample g had an average particle size according to ERT 420.2-02 of 524 μm. The water content of sample g determined according to ERT 430.1-99 was 4.4%.

Example 10

Preparation of a Post-crosslinked Agglomerated Water-absorbing Polymer Structure with Zinc Ricinolate—Sample h Example 9 was followed, with the difference that before the addition of the binder to the mixture, 1%, based on the mixture, of zinc ricinolate as Tegosorb® A30 was mixed in to the aqueous binder phase. The thus-obtained sample h had an average particle size according to ERT 420.2-02 of 523 μm. The water content of sample h determined according to ERT 430.1-99 was 4.5%.

Example 11

Superabsorbing Compositions—Odor Binder on Post-crosslinked Superabsorbing Polymer—Samples i1 to i5

100 dry weight parts of sample c were provided and combined with the amounts given in Table 4 (based on the dry weight parts) of odor binder and homogenized in an MIT mixer type LM 1.5/5 from the company Mischtechnik Industrieanlagen GmbH. The results of the analyses are shown in Table 4.

TABLE 4

| | (respectively determined three times) | | |
| --- | --- | --- | --- |
| Sample | Zn-Ricinolate [%] | AAP 0,7 [g/g] | Surface tension [mN/m] | Wicking-Index [mm] |
| g | 0 | 10.8 | 71.0 | 165 |
| h | 1 | 7.7 (−28%) | 39.2 (−45%) | 90 (−45.5%) |
| i1 | 0 | 25.9 | 69.3 | 230 |
| i2 | 0.1 | 24.8 | 41.5 | 165 |
| i3 | 0.3 | 25.2 | 40.9 | 165 |
| i4 | 0.5 | 24.9 | 41.1 | 160 |
| i5 | 1 | 23.9 (−7.7%) | 39.9 (−42.5%) | 170 (−26%) |

The invention claimed is:
1. An odor-absorbing superabsorbing composition, comprising:
   i a post-crosslinked water-absorbing polymer structure having an average particle size in the range of about 515 μm to about 850 μm; and
   ii an odor binder comprising as components
      b1 an amino acid wherein said amino acid is cysteine; and
      b2 a ricinolate compound of general formula I

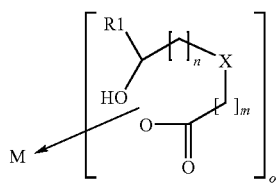

formula I with
R1 as a $C_1$ to $C_{20}$ hydrocarbon,
X as not present or a double bond system comprising in a range from 1 to about 5 double bonds;
M as a charged or uncharged metal;
m in a range from 1 to about 15;
n in a range from 1 to about 5;
o in a range from 1 to about 4,
wherein said odor binder is brought into contact with the surface of the post-crosslinked water-absorbing polymer structure after surface crosslinking such that the penetration depth of said odor binder into said surface of the post-crosslinked water-absorbing polymer structure is less than 2% of the diameter of the water-absorbing polymer structure wherein the odor-absorbing superabsorbing composition has an absorption against pressure of 0.7 psi (AAP(0.7 psi)) of from 21 g/g to 30 g/g.

2. The odor-absorbing superabsorbing composition according to claim 1, wherein the ricinolate compound is zinc ricinolate.

3. The odor-absorbing superabsorbing composition according to claim 1, further comprising less than 20 wt. %, based on the odor-absorbing superabsorbing composition, of a cross-linkable, non-crosslinked polymer.

4. The odor-absorbing superabsorbing composition according to claim 1 wherein the post-crosslinked water-absorbing polymer structure is surface crosslinked with a compound which is different from component b1.

5. The odor-absorbing superabsorbing composition according to claim 1 further comprising iii. a polymeric binder which is different from the post-crosslinked water-absorbing polymer structure.

6. The odor-absorbing superabsorbing composition according to claim 5, whereby the polymeric binder comprises two or more OH groups.

7. A composite comprising the odor-absorbing superabsorbing composition according to claim 1.

8. A hygiene article comprising a liquid-permeable top sheet, a liquid impermeable back sheet and a composite according to claim 7 arranged between the top sheet and the back sheet.

9. A process for production of a superabsorbing composition, comprising the process steps of:
  i providing a post-crosslinked water-absorbing polymer structure having an average particle size in the range of about 515 μm to about 850 μm; and;
  ii bringing into contact of the surface of the post-crosslinked water-absorbing polymer structure with an odor binder comprising as components
    b1 an amino acid wherein said amino acid is cysteine; and
    b2 a ricinolate compound of general formula I

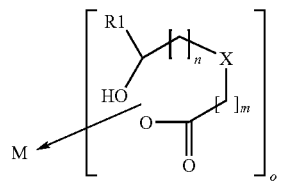

formula I with
R1 as a $C_1$ to $C_{20}$ hydrocarbon;
X as not present or a double bond system comprising in a range from 1 to 5 double bonds;
M as a charged or uncharged metal;
m in a range from 1 to about 15;
n in a range from 1 to about 5;
o in a range from 1 to about 4
wherein said odor binder is brought into contact with the surface of the post-crosslinked water-absorbing polymer structure after surface crosslinking such that the penetration depth of said odor binder into said surface of the post-crosslinked water-absorbing polymer structure is less than 2% of the diameter of the water-absorbing polymer structure wherein the odor-absorbing superabsorbing composition has an absorption against pressure of 0.7 psi (AAP(0.7 psi)) of from 21 g/g to 30 g/g.

10. The process according to claim 9 wherein the ricinolate compound is zinc ricinolate.

11. The process according to claim 9 wherein the water-absorbing polymer structure has a water content of less than 10 wt. %, based on the polymer structure.

12. The process according to claim 9 wherein less than 20 wt. %, based on the composition, of a cross-linkable, non-crosslinked polymer is used as a binder.

* * * * *